(12) United States Patent
Esfandiari

(10) Patent No.: US 11,350,913 B2
(45) Date of Patent: Jun. 7, 2022

(54) METHOD AND APPARATUS FOR COLLECTING AND PREPARING BIOLOGICAL SAMPLES FOR TESTING

(71) Applicant: Chembio Diagnostic Systems, Inc., Medford, NY (US)

(72) Inventor: Javanbakhsh Esfandiari, Stony Brook, NY (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 398 days.

(21) Appl. No.: 16/373,445

(22) Filed: Apr. 2, 2019

(65) Prior Publication Data

US 2019/0261961 A1     Aug. 29, 2019

Related U.S. Application Data

(60) Division of application No. 13/055,536, filed as application No. PCT/US2009/051335 on Jul. 22, 2009, now abandoned, which is a continuation-in-part of application No. 12/179,248, filed on Jul. 24, 2008, now abandoned.

(51) Int. Cl.
*A61B 10/00*      (2006.01)
*A61B 5/15*      (2006.01)

(52) U.S. Cl.
CPC .... *A61B 10/0045* (2013.01); *A61B 5/150015* (2013.01); *A61B 5/150305* (2013.01); *A61B 5/150351* (2013.01); *A61B 5/150755* (2013.01); *A61B 2010/0006* (2013.01)

(58) Field of Classification Search
CPC .......... A61B 10/0045; A61B 5/150015; A61B 5/150305; A61B 5/150351; A61B 5/150755; A61B 2010/0006; A61B 10/0096; A61B 10/0051; Y10S 436/81; Y10S 435/81; G01N 33/558; B01L 3/5023; B01L 3/5029
See application file for complete search history.

(56) References Cited

U.S. PATENT DOCUMENTS

| | | |
|---|---|---|
| 3,815,580 A | 6/1974 | Oster |
| 3,960,488 A | 6/1976 | Giaever |
| 4,041,146 A | 8/1977 | Giaever |
| 4,042,335 A | 8/1977 | Clement |
| 4,059,405 A | 11/1977 | Sodickson et al. |
| 4,094,647 A | 6/1978 | Deutsch et al. |
| 4,144,306 A | 3/1979 | Figueras |
| 4,235,601 A | 11/1980 | Deutsch et al. |
| 4,323,536 A | 4/1982 | Columbus |
| 4,361,537 A | 11/1982 | Deutsch et al. |
| 4,522,786 A | 6/1985 | Ebersole |
| 4,532,107 A | 7/1985 | Siddigi |
| 4,588,555 A | 5/1986 | Provonchee |
| 4,595,654 A | 6/1986 | Reckel et al. |
| 4,632,901 A | 12/1986 | Valkirs et al. |

(Continued)

OTHER PUBLICATIONS

International Search Report of International Application No. PCT/US 09/51335 dated Sep. 1, 2009.

*Primary Examiner* — Patrick Fernandes
(74) *Attorney, Agent, or Firm* — Gordon & Jacobson, P.C.

(57) ABSTRACT

A kit and a method are disclosed for collecting and preparing a biological sample for testing where the sample is to be mixed with a buffer prior to being tested.

11 Claims, 7 Drawing Sheets

(56) References Cited

U.S. PATENT DOCUMENTS

| | | |
|---|---|---|
| 4,668,619 A | 5/1987 | Greenquist et al. |
| 4,740,468 A | 4/1988 | Weng et al. |
| 4,785,796 A | 11/1988 | Mattson |
| 4,786,595 A | 11/1988 | Arai et al. |
| 4,803,998 A * | 2/1989 | Kezes ............... A61B 10/0096 435/307.1 |
| 4,826,759 A | 5/1989 | Guire et al. |
| 4,855,240 A | 8/1989 | Rosenstein et al. |
| 4,857,453 A | 8/1989 | Ullman et al. |
| 4,870,003 A | 9/1989 | Kortright et al. |
| 4,886,742 A | 12/1989 | Kortright et al. |
| 4,906,439 A | 3/1990 | Grenner |
| 4,912,034 A | 3/1990 | Kalra et al. |
| 4,920,046 A | 4/1990 | McFarland et al. |
| 4,943,522 A | 7/1990 | Eisinger et al. |
| 4,956,275 A | 9/1990 | Zuk et al. |
| 4,956,302 A | 9/1990 | Gordon et al. |
| 4,960,691 A | 10/1990 | Gordon et al. |
| 4,960,710 A | 10/1990 | Lau |
| 4,981,785 A | 1/1991 | Nayak |
| 4,981,786 A | 1/1991 | Dafforn et al. |
| 5,004,584 A | 4/1991 | Rayman |
| 5,006,464 A | 4/1991 | Chu et al. |
| 5,006,474 A | 4/1991 | Horstman et al. |
| 5,075,077 A | 12/1991 | Durley, III et al. |
| 5,087,556 A | 2/1992 | Ertinghausen |
| 5,091,153 A | 2/1992 | Bachand |
| 5,104,793 A | 4/1992 | Buck |
| 5,104,811 A | 4/1992 | Berger et al. |
| 5,110,550 A | 5/1992 | Schlipfenbacher et al. |
| 5,132,208 A | 7/1992 | Freitag et al. |
| 5,137,808 A | 8/1992 | Ullman et al. |
| 5,147,780 A | 9/1992 | Pouletty et al. |
| 5,156,952 A | 10/1992 | Litman et al. |
| 5,162,238 A | 10/1992 | Eikmeier et al. |
| 5,169,789 A | 12/1992 | Bernstein |
| 5,173,433 A | 12/1992 | Bachand |
| 5,200,321 A | 4/1993 | Kidwell |
| 5,202,268 A | 4/1993 | Kuhn et al. |
| 5,217,905 A | 6/1993 | Marchand et al. |
| 5,219,762 A | 6/1993 | Katamine et al. |
| 5,223,436 A | 6/1993 | Freitag et al. |
| RE34,312 E | 7/1993 | Geiger et al. |
| 5,232,835 A | 8/1993 | Litman et al. |
| 5,238,649 A | 8/1993 | Nason |
| 5,240,735 A | 8/1993 | Lau |
| 5,244,631 A | 9/1993 | Morikawa |
| 5,244,788 A | 9/1993 | Hubscher |
| RE34,405 E | 10/1993 | Gould et al. |
| 5,275,785 A | 1/1994 | May et al. |
| 5,281,540 A | 1/1994 | Merkh et al. |
| 5,296,192 A | 3/1994 | Carroll et al. |
| 5,300,439 A | 4/1994 | Charlton |
| 5,306,623 A | 4/1994 | Kiser et al. |
| 5,308,775 A | 5/1994 | Donovan et al. |
| 5,320,809 A | 6/1994 | Dunn et al. |
| 5,328,058 A | 7/1994 | Leoncavallo et al. |
| 5,332,548 A | 7/1994 | Moore |
| 5,334,502 A | 8/1994 | Sangha |
| 5,338,513 A | 8/1994 | Schllipfenbacher et al. |
| 5,340,748 A | 8/1994 | Baugher et al. |
| 5,356,782 A | 10/1994 | Moorman et al. |
| 5,362,654 A | 11/1994 | Pouletty |
| 5,369,007 A | 11/1994 | Kidwell |
| 5,384,264 A | 1/1995 | Chen et al. |
| 5,391,478 A | 2/1995 | Greene et al. |
| 5,399,316 A | 3/1995 | Yamada |
| 5,411,858 A | 5/1995 | McGeehan et al. |
| 5,418,136 A | 5/1995 | Miller et al. |
| 5,418,142 A | 5/1995 | Kiser et al. |
| 5,418,167 A | 5/1995 | Matner et al. |
| 5,424,215 A | 6/1995 | Albarella et al. |
| 5,424,220 A | 6/1995 | Goerlach-Graw et al. |
| 5,435,970 A | 7/1995 | Mamenta et al. |
| 5,451,504 A | 9/1995 | Fitzpatrick et al. |
| 5,468,648 A | 11/1995 | Chandler |
| 5,470,713 A | 11/1995 | El Shami et al. |
| 5,474,902 A | 12/1995 | Uylen et al. |
| 5,477,863 A | 12/1995 | Grant |
| 5,482,830 A | 1/1996 | Bpogart et al. |
| 5,494,830 A | 2/1996 | Hubscher |
| 5,500,350 A | 3/1996 | Baker et al. |
| 5,501,985 A | 3/1996 | Baugher et al. |
| 5,514,557 A | 5/1996 | Moghaddam |
| 5,521,102 A | 5/1996 | Boehringer et al. |
| 5,532,133 A | 7/1996 | Barnwell |
| 5,541,057 A | 7/1996 | Bogart et al. |
| 5,543,115 A | 8/1996 | Karakawa |
| 5,550,063 A | 8/1996 | Bogart |
| 5,552,272 A | 9/1996 | Bogart |
| 5,558,834 A | 9/1996 | Chu et al. |
| 5,559,041 A | 9/1996 | Kang et al. |
| 5,567,594 A | 10/1996 | Calenoff |
| 5,571,667 A | 11/1996 | Chu et al. |
| 5,591,645 A | 1/1997 | Rosenstein |
| 5,602,040 A | 2/1997 | May et al. |
| 5,604,110 A | 2/1997 | Baker et al. |
| 5,607,863 A | 3/1997 | Chandler |
| 5,616,467 A | 4/1997 | Olsen et al. |
| 5,620,845 A | 4/1997 | Gould et al. |
| 5,622,871 A | 4/1997 | May et al. |
| 5,623,942 A | 4/1997 | Pestes et al. |
| 5,624,809 A | 4/1997 | Skold et al. |
| 5,629,164 A | 5/1997 | Rivers |
| 5,629,214 A | 5/1997 | Crosby |
| 5,639,671 A | 6/1997 | Bogart et al. |
| 5,641,639 A | 6/1997 | Perry |
| 5,648,274 A | 7/1997 | Chandler |
| 5,656,503 A | 8/1997 | May et al. |
| 5,658,801 A | 8/1997 | Poissant et al. |
| 5,670,381 A | 9/1997 | Jou et al. |
| 5,686,315 A | 11/1997 | Pronovost et al. |
| 5,695,928 A | 12/1997 | Stewart |
| 5,695,930 A | 12/1997 | Weinstein et al. |
| 5,710,005 A | 1/1998 | Rittenburg |
| 5,714,341 A | 2/1998 | Thieme et al. |
| 5,714,389 A | 2/1998 | Charlton et al. |
| 5,723,345 A | 3/1998 | Yamauchi et al. |
| 5,726,010 A | 3/1998 | Clark |
| 5,728,587 A | 3/1998 | Kang et al. |
| 5,739,041 A | 4/1998 | Nazareth et al. |
| 5,750,333 A | 5/1998 | Clark |
| 5,766,961 A | 6/1998 | Pawlak et al. |
| 5,766,962 A | 6/1998 | Childs et al. |
| 5,770,460 A | 6/1998 | Pawlak et al. |
| 5,773,234 A | 6/1998 | Pronovost et al. |
| 5,786,220 A | 7/1998 | Pronovost et al. |
| 5,807,756 A | 9/1998 | Bauman et al. |
| 5,814,522 A | 9/1998 | Zimmer et al. |
| 5,824,268 A | 10/1998 | Bernstein et al. |
| 5,827,646 A | 10/1998 | Middledorp et al. |
| 5,846,838 A | 12/1998 | Chandler |
| 5,853,670 A | 12/1998 | Bunce |
| 5,861,265 A | 1/1999 | Perry |
| 5,869,272 A | 2/1999 | Bogart et al. |
| 5,869,345 A | 2/1999 | Chandler |
| 5,872,713 A | 2/1999 | Douglas et al. |
| 5,874,216 A | 2/1999 | Mapes |
| 5,877,028 A | 3/1999 | Chandler et al. |
| 5,879,951 A | 3/1999 | Sy |
| 5,885,526 A | 3/1999 | Chu |
| 5,885,527 A | 3/1999 | Buechler |
| 5,891,650 A | 4/1999 | Godowski et al. |
| 5,900,379 A | 5/1999 | Noda et al. |
| 5,902,722 A | 5/1999 | Di Cesare et al. |
| 5,912,116 A | 6/1999 | Caldwell |
| 5,922,533 A | 7/1999 | Vallari et al. |
| 5,922,615 A | 7/1999 | Nowakowski et al. |
| 5,928,176 A | 7/1999 | Nakatani |
| 5,939,252 A | 8/1999 | Lennon et al. |
| 5,939,272 A | 8/1999 | Buechler et al. |
| 5,948,695 A | 9/1999 | Douglas et al. |
| 5,955,377 A | 9/1999 | Maul et al. |
| 5,958,790 A | 9/1999 | Cerny |

(56) References Cited

U.S. PATENT DOCUMENTS

| | | |
|---|---|---|
| 5,965,458 A | 10/1999 | Kouvonen et al. |
| 5,972,720 A | 10/1999 | Nicht et al. |
| 5,976,895 A | 11/1999 | Cipkowski |
| 5,985,675 A | 11/1999 | Charm et al. |
| 5,989,921 A | 11/1999 | Charlton et al. |
| 5,998,220 A | 12/1999 | Chandler |
| 5,998,221 A | 12/1999 | Malick et al. |
| 6,008,056 A | 12/1999 | Thieme |
| 6,017,767 A | 1/2000 | Chandler |
| 6,027,890 A | 2/2000 | Ness et al. |
| 6,040,195 A | 3/2000 | Carroll et al. |
| 6,046,013 A | 4/2000 | Tidey et al. |
| 6,046,057 A | 4/2000 | Nazareth et al. |
| 6,057,166 A | 5/2000 | Childs et al. |
| 6,060,326 A | 5/2000 | Frank et al. |
| 6,063,337 A | 5/2000 | Markart |
| 6,087,184 A | 7/2000 | Magginetti et al. |
| 6,106,732 A | 8/2000 | Johnston et al. |
| 6,140,134 A | 10/2000 | Rittenburg |
| 6,140,136 A | 10/2000 | Lee |
| 6,168,956 B1 | 1/2001 | Chandler |
| 6,171,260 B1 | 1/2001 | Hochmeister et al. |
| 6,187,268 B1 | 2/2001 | Albarella et al. |
| 6,187,598 B1 | 2/2001 | May et al. |
| 6,194,220 B1 | 2/2001 | Malilck et al. |
| 6,197,494 B1 | 3/2001 | Oberhardt |
| 6,221,625 B1 | 4/2001 | Ashihara et al. |
| 6,221,678 B1 | 4/2001 | Chandler |
| 6,224,831 B1 | 5/2001 | Stafford et al. |
| 6,228,660 B1 | 5/2001 | May et al. |
| 6,235,464 B1 | 5/2001 | Henderson et al. |
| 6,248,598 B1 | 6/2001 | Bogema |
| 6,258,548 B1 | 7/2001 | Buck |
| 6,271,040 B1 | 8/2001 | Buechler |
| 6,271,045 B1 | 8/2001 | Douglas et al. |
| 6,271,046 B1 | 8/2001 | Chandler |
| 6,277,650 B1 | 8/2001 | Nazareth et al. |
| 6,284,550 B1 | 9/2001 | Carroll et al. |
| 6,287,875 B1 | 9/2001 | Geisberg |
| 6,297,020 B1 | 10/2001 | Brock |
| 6,297,060 B1 | 10/2001 | Nowakowski et al. |
| 6,300,142 B1 | 10/2001 | Andrewes et al. |
| RE37,437 E | 11/2001 | Friesen et al. |
| 6,316,205 B1 | 11/2001 | Guan et al. |
| 6,316,264 B1 | 11/2001 | Corey et al. |
| 6,319,676 B1 | 11/2001 | Nazareth et al. |
| 6,326,214 B1 | 12/2001 | Liu et al. |
| 6,335,205 B1 | 1/2002 | Bausback |
| 6,352,862 B1 | 3/2002 | Davis et al. |
| 6,362,008 B1 | 3/2002 | Kohn et al. |
| 6,368,875 B1 | 4/2002 | Geisberg |
| 6,368,876 B1 | 4/2002 | Huang et al. |
| 6,372,514 B1 | 4/2002 | Lee |
| 6,372,515 B1 | 4/2002 | Casterlin et al. |
| 6,372,516 B1 | 4/2002 | Sun |
| 6,376,195 B1 | 4/2002 | Mapes |
| 6,383,804 B1 | 5/2002 | Ward, Jr. et al. |
| 6,399,398 B1 | 6/2002 | Cunningham et al. |
| 6,403,383 B1 | 6/2002 | Casterlin et al. |
| 6,403,384 B1 | 6/2002 | Lea |
| 6,406,922 B2 | 6/2002 | Casterlin et al. |
| 6,413,473 B1 | 7/2002 | Bacon |
| 6,413,784 B1 | 7/2002 | Lundsgaard et al. |
| 6,436,722 B1 | 8/2002 | Clark et al. |
| 6,455,324 B1 | 9/2002 | Douglas |
| 6,472,226 B1 | 10/2002 | Barradine et al. |
| 6,475,805 B1 | 11/2002 | Charm et al. |
| 6,485,982 B1 | 11/2002 | Charlton |
| 6,489,129 B1 | 12/2002 | Faatz et al. |
| 6,492,127 B2 | 12/2002 | Goodell et al. |
| 6,500,629 B1 | 12/2002 | Cleaver et al. |
| 6,503,702 B1 | 1/2003 | Stewart |
| 6,503,722 B1 | 1/2003 | Valkirs |
| 6,511,814 B1 | 1/2003 | Carpenter |
| 6,514,769 B2 | 2/2003 | Lee |
| 6,514,773 B1 | 2/2003 | Klein et al. |
| 6,528,321 B1 | 3/2003 | Fitzgerald et al. |
| 6,528,322 B1 | 3/2003 | Carlsson et al. |
| 6,528,323 B1 | 3/2003 | Thayer et al. |
| 6,528,325 B1 | 3/2003 | Hubscher et al. |
| 6,534,324 B1 | 3/2003 | Zin |
| 6,544,474 B2 | 4/2003 | Douglas |
| 6,548,309 B1 | 4/2003 | Moore et al. |
| 6,551,842 B1 | 4/2003 | Carpenter |
| 6,592,815 B1 | 7/2003 | Zimmer |
| 6,593,085 B1 | 7/2003 | Barnett et al. |
| 6,602,719 B1 | 8/2003 | Carpenter |
| 6,617,116 B2 | 9/2003 | Guan et al. |
| 6,623,955 B2 | 9/2003 | Matner et al. |
| 6,627,459 B1 | 9/2003 | Tung et al. |
| 6,632,202 B1 | 10/2003 | Hagele |
| 6,632,681 B1 | 10/2003 | Chu |
| 6,645,732 B2 | 11/2003 | Faatz et al. |
| 6,649,418 B1 | 11/2003 | Geisberg |
| 6,656,744 B2 | 12/2003 | Pronovost et al. |
| 6,656,745 B1 | 12/2003 | Cole |
| 6,660,469 B1 | 12/2003 | Wright et al. |
| 6,663,833 B1 | 12/2003 | Stave et al. |
| 6,673,628 B2 | 1/2004 | Freitag et al. |
| RE38,430 E | 2/2004 | Rosenstein |
| 6,686,167 B2 | 2/2004 | Bagaria |
| 6,699,722 B2 | 3/2004 | Bauer et al. |
| 6,703,196 B1 | 3/2004 | Klepp et al. |
| 6,706,539 B2 | 3/2004 | Nelson et al. |
| 6,713,309 B1 | 3/2004 | Anderson et al. |
| 6,727,073 B1 | 4/2004 | Moore et al. |
| 6,737,277 B1 | 5/2004 | Kang et al. |
| 6,750,031 B1 | 6/2004 | Ligler et al. |
| 6,753,190 B1 | 6/2004 | Okada et al. |
| 6,767,710 B2 | 7/2004 | DiNello et al. |
| 6,767,714 B2 | 7/2004 | Nazareth et al. |
| 6,780,651 B2 | 8/2004 | Douglas et al. |
| 6,790,611 B2 | 9/2004 | Lassen et al. |
| 6,797,481 B1 | 9/2004 | Ullman et al. |
| 6,808,889 B2 | 10/2004 | Fitzpatrick et al. |
| 6,808,937 B2 | 10/2004 | Ligler et al. |
| 6,812,038 B1 | 11/2004 | Mendel-Hartvig et al. |
| 6,818,180 B2 | 11/2004 | Douglas et al. |
| 6,818,455 B2 | 11/2004 | May et al. |
| 6,824,975 B2 | 11/2004 | Hubscher et al. |
| 6,824,997 B1 | 11/2004 | Moore et al. |
| 6,828,110 B2 | 12/2004 | Le et al. |
| RE38,688 E | 1/2005 | Friesen et al. |
| 6,844,200 B2 | 1/2005 | Brock |
| 6,846,635 B1 | 1/2005 | Anderson et al. |
| 6,849,414 B2 | 2/2005 | Guan et al. |
| 6,855,561 B2 | 2/2005 | Jerome et al. |
| 6,863,866 B2 | 3/2005 | Kelly et al. |
| 6,867,051 B1 | 3/2005 | Anderson et al. |
| 6,887,701 B2 | 5/2005 | Anderson et al. |
| 6,905,835 B2 | 6/2005 | Gomez et al. |
| 6,924,153 B1 | 8/2005 | Boehringer et al. |
| 6,927,068 B2 | 8/2005 | Simonson et al. |
| 6,991,940 B2 | 1/2006 | Carroll et al. |
| 7,018,847 B2 | 3/2006 | Mendel-Hartvig et al. |
| 7,045,342 B2 | 5/2006 | Nazareth et al. |
| 7,049,130 B2 | 5/2006 | Carroll et al. |
| 7,109,042 B2 | 9/2006 | May et al. |
| 7,175,057 B2 | 2/2007 | Mutterle |
| 7,178,703 B2 | 2/2007 | Spada et al. |
| 7,189,522 B2 | 3/2007 | Esfandiari |
| 7,374,949 B2 | 5/2008 | Kuriger |
| 2001/0007926 A1 | 7/2001 | Trudil |
| 2001/0012637 A1 | 8/2001 | Casterlin et al. |
| 2001/0026942 A1 | 10/2001 | Carpenter et al. |
| 2001/0026944 A1 | 10/2001 | Chung et al. |
| 2001/0034068 A1 | 10/2001 | Spivey et al. |
| 2001/0039057 A1 | 11/2001 | Douglas et al. |
| 2001/0048893 A1 | 12/2001 | Norris et al. |
| 2002/0001853 A1 | 1/2002 | Obremski et al. |
| 2002/0015663 A1 | 2/2002 | Goldstein et al. |
| 2002/0019062 A1 | 2/2002 | Lea et al. |
| 2002/0031839 A1 | 3/2002 | McNeirney et al. |
| 2002/0046614 A1 | 4/2002 | Alley |

(56) References Cited

U.S. PATENT DOCUMENTS

| | | |
|---|---|---|
| 2002/0048819 A1 | 4/2002 | Alley |
| 2002/0052050 A1 | 5/2002 | Douglas et al. |
| 2002/0057991 A1 | 5/2002 | Kelly et al. |
| 2002/0058330 A1 | 5/2002 | Carroll et al. |
| 2002/0110803 A1 | 8/2002 | Dhar et al. |
| 2002/0119497 A1 | 8/2002 | Wild et al. |
| 2002/0142291 A1 | 10/2002 | Bauer et al. |
| 2002/0155028 A1 | 10/2002 | Wong |
| 2002/0173050 A1 | 11/2002 | DiNello et al. |
| 2002/0192839 A1 | 12/2002 | Mink et al. |
| 2003/0045001 A1 | 3/2003 | Burgess et al. |
| 2003/0118480 A1 | 6/2003 | Kaylor et al. |
| 2003/0124740 A1 | 7/2003 | Bachand |
| 2003/0138351 A1 | 7/2003 | Etes et al. |
| 2003/0138971 A1 | 7/2003 | D'Aurora |
| 2003/0143639 A1 | 7/2003 | Matsushita et al. |
| 2003/0180967 A1 | 9/2003 | Shigetoh |
| 2003/0199004 A1 | 10/2003 | Fong |
| 2004/0014237 A1* | 1/2004 | Sugiyama .......... B01L 3/50825 436/174 |
| 2004/0087036 A1 | 5/2004 | Chung et al. |
| 2004/0142495 A1 | 7/2004 | Hartman et al. |
| 2004/0161859 A1 | 8/2004 | Guo et al. |
| 2004/0170536 A1 | 9/2004 | Daykin |
| 2004/0184954 A1 | 9/2004 | Guo et al. |
| 2004/0219694 A1 | 11/2004 | Chittock et al. |
| 2004/0235189 A1 | 11/2004 | Lu |
| 2004/0241779 A1 | 12/2004 | Paisio et al. |
| 2004/0248322 A1 | 12/2004 | Charlton |
| 2005/0059161 A1* | 3/2005 | Anderson .......... G01N 35/1079 436/174 |
| 2005/0074900 A1 | 4/2005 | Morgan et al. |
| 2005/0079629 A1 | 4/2005 | Guo et al. |
| 2005/0106753 A1* | 5/2005 | Wu ....................... B01L 3/5029 436/180 |
| 2005/0112779 A1 | 5/2005 | Wei et al. |
| 2005/0112780 A1 | 5/2005 | Song |
| 2005/0112782 A1 | 5/2005 | Buechler |
| 2005/0130293 A1 | 6/2005 | Blatt et al. |
| 2005/0130310 A1 | 6/2005 | Wandell et al. |
| 2005/0130319 A1 | 6/2005 | Biegelsen et al. |
| 2005/0136500 A1 | 6/2005 | Yang et al. |
| 2005/0142032 A1 | 6/2005 | Hoenes et al. |
| 2005/0164404 A1 | 7/2005 | Marlborugh et al. |
| 2005/0170527 A1 | 8/2005 | Boehringer et al. |
| 2005/0208677 A1 | 9/2005 | Owens et al. |
| 2005/0227371 A1 | 10/2005 | Gokhan |
| 2005/0232813 A1 | 10/2005 | Karmali |
| 2005/0244985 A1 | 11/2005 | Freitag et al. |
| 2005/0244986 A1 | 11/2005 | May et al. |
| 2006/0099719 A1 | 5/2006 | Curcio |
| 2006/0115385 A1 | 6/2006 | Jon Meyer |
| 2006/0121626 A1 | 6/2006 | Imrich |
| 2006/0134803 A1 | 6/2006 | Esfandiari |
| 2006/0205059 A1* | 9/2006 | Esfandiari .......... G01N 33/5695 435/287.2 |
| 2006/0245977 A1 | 11/2006 | Bodner |
| 2007/0167900 A1 | 7/2007 | Kanjilal et al. |
| 2007/0208275 A1 | 9/2007 | Vinogradov et al. |
| 2007/0299364 A1 | 12/2007 | Sangha |
| 2008/0139962 A1 | 6/2008 | Jehlani et al. |
| 2008/0254550 A1 | 10/2008 | Nathaniel |
| 2009/0004688 A1 | 1/2009 | McIver |
| 2009/0156962 A1 | 6/2009 | Yong |
| 2009/0311032 A1 | 12/2009 | Kurek |

* cited by examiner

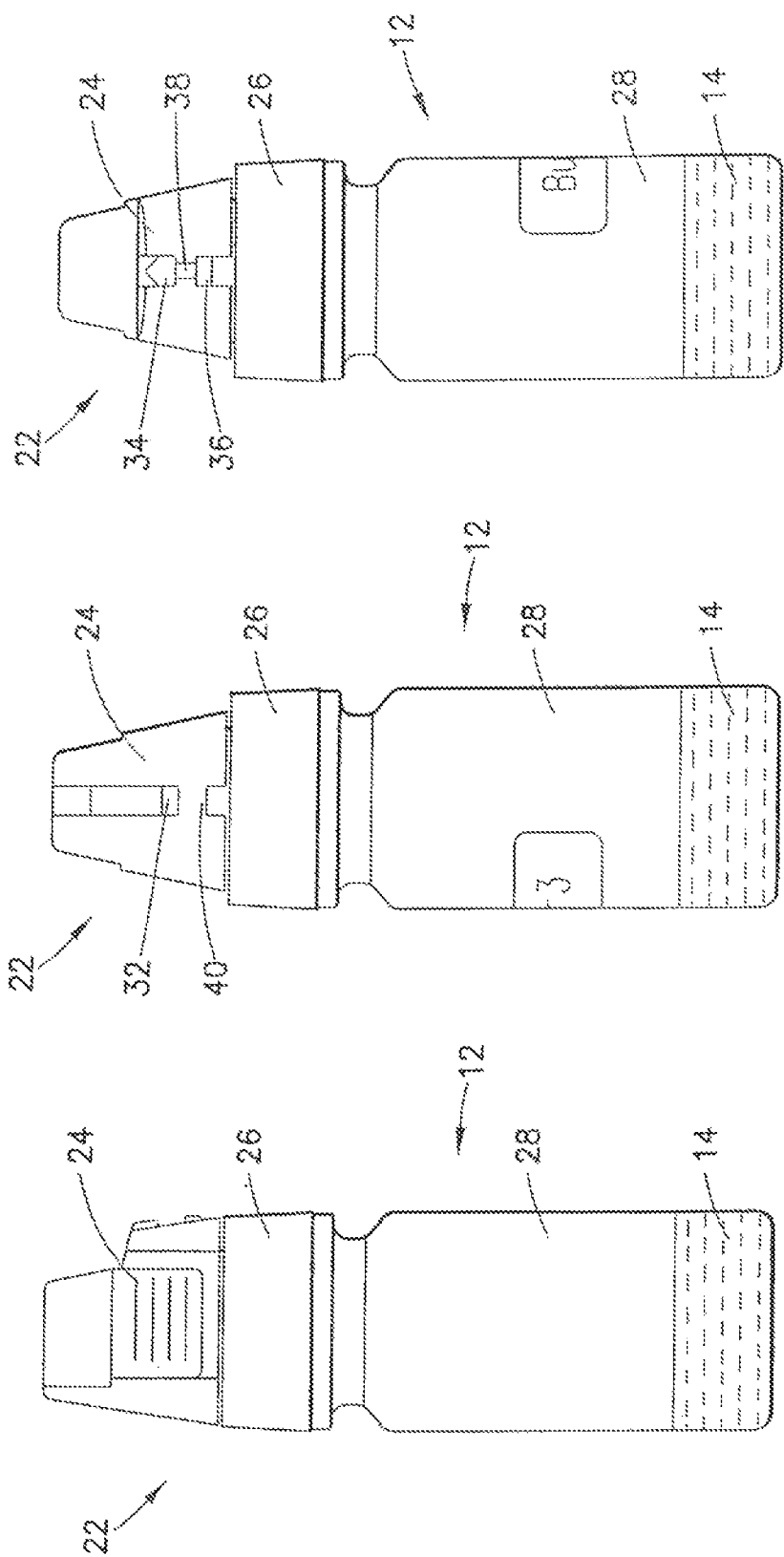

METHOD AND APPARATUS FOR COLLECTING AND PREPARING BIOLOGICAL SAMPLES FOR TESTING

CROSS-REFERENCE TO RELATED APPLICATIONS

This application is a divisional of U.S. Ser. No. 13/055,536, filed Mar. 31, 2011, which is a 371 national phase application of PCT/US09/51335, filed Jul. 22, 2009, which is a continuation-in-part of U.S. Ser. No. 12/179,248, filed Jul. 24, 2008, all of which are hereby incorporated by reference herein in their entireties. This application is related to co-owned U.S. Pat. No. 7,189,522, entitled "Dual Path Immunoassay Device," the complete disclosure of which is hereby incorporated by reference herein.

BACKGROUND OF THE INVENTION

1. Field of the Invention

This invention relates broadly to the testing of biological samples such as blood, oral fluids, epithelia, urine, stool, etc. More particularly, this invention relates to methods and apparatus for collecting and preparing such samples prior to testing.

2. State of the Art

Many types of ligand-receptor assays have been used to detect the presence of various substances, often generally called ligands, in body fluids such as blood, urine, or saliva. These assays involve antigen antibody reactions, synthetic conjugates comprising radioactive, enzymatic, fluorescent, or visually observable polystyrene or metal sol tags, and specially designed reactor chambers. In all these assays, there is a receptor, e.g., an antibody, which is specific for the selected ligand or antigen, and a means for detecting the presence, and in some cases the amount, of the ligand-receptor reaction product. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

U.S. Pat. No. 6,485,982 discloses what may be called a single path immunoassay device. The device has an elongate outer casing which houses an interior permeable material, e.g., glass fiber, capable of transporting an aqueous solution by capillary action, wicking, or simple wetting. The casing defines a sample inlet, and interior regions which, for ease of description, can be designated as a test volume and a reservoir volume. The reservoir volume is disposed in a section of the test cell spaced apart from the inlet, and preferably is filled with sorbent material. The reservoir acts to receive liquid transported along a flow path defined by the permeable material and extending from the inlet and through the test volume. In the test volume is a test site comprising a first protein having a binding site specific to a first epitope of the ligand immobilized in fluid communication with the flow path, e.g., bound to the permeable material or to latex particles entrapped in or bonded to the permeable material. A window such as a hole or transparent section of the casing permits observations of the test site through the casing wall. The method requires that the test sample be mixed with a conjugate or buffer before it is dispensed into the inlet.

Previously incorporated U.S. Pat. No. 7,189,522 discloses both dry and liquid conjugate immunoassay device systems. The systems include test cells with a first sorbent having a first location for receiving a buffer solution (in the case of a dry conjugate system) or a conjugate solution (in the case of a liquid conjugate system) with the first sorbent defining a first horizontal flow path, a second sorbent having a second location for receiving a sample with the second sorbent defining a second horizontal flow path distinct from the first flow path, and a test line or test site with immobilized antigens or antibodies or other ligand binding molecules such as aptamers, nucleic acids, etc. located in a test zone at a junction of the first and second sorbents.

Where the test cell is provided in a housing, such as the housing 1 show in prior art FIG. 1, the housing is provided with a first opening 2 adjacent the first location and a second opening 3 adjacent the second location. A viewing window 4 is provided in the housing above the test line 5.

In the preferred embodiment, the first sorbent and second sorbent are separate pieces which overlie one another and the test line is printed on one or both of the sorbent materials at the junction. Alternatively, although not preferred, the first and second sorbents can be integral with each other. The systems preferably also include a control line 6 or site which may be seen from the viewing window 4.

According to one set of embodiments, the sorbents (and the housing in which the sorbents are provided) are laid out in a T shape, where the first location 2 for receiving the buffer or buffer-conjugate solution is located near one end of the top bar of the T, the second location 3 for receiving the sample is located near the end of the stem of the T, and the sorbents overlie each other at the intersection.

According to one disclosed method, a sample of interest is provided to the second opening or location 3. After a desired amount of time, a liquid such as a buffer solution is added to the first opening or location 2. If the sorbent is supporting a conjugate (i.e., in a dry conjugate system), the liquid is preferably simply a buffer solution. If the sorbent is not supporting a conjugate (i.e., in a liquid conjugate system), the liquid is preferably a buffer-conjugate liquid subsystem. In any event, after sufficient time to permit the conjugate to migrate to the test site 5 (and control site 6 if provided), the test site (and control site if provided) is inspected in order to determine whether the sample is "positive" or not.

The disclosed system can be used in conjunction with different types of samples such as blood, urine, saliva, and feces, and can be used to test for the presence of any ligand. Where blood, saliva or feces is to be provided, the blood, saliva or feces may be diluted or mixed with buffer prior to being added through the second hole 3. Alternatively, in some cases, the sample may be added through the hole and then a diluent may be added through the same hole 3.

SUMMARY OF THE INVENTION

The present invention provides a kit and a method for collecting and preparing a biological sample for use with an immunoassay device where the sample is to be mixed with a buffer prior to being added to the device. The kit includes a sterile swab and a dropper bottle assembly containing the buffer solution to which the sample is added. In one embodiment, the dropper bottle assembly includes a dropper cap having a hinged cover and a threaded base and a bottle having a threaded neck. When the kit is delivered for use, the dropper cap is threadably connected to the threaded neck of the bottle and the hinged cover is closed. The sterile swab includes a sorbent mounted on the end of a stick. The stick is preferably long enough so that a sample can be obtained without the person taking the sample contaminating it. The stick is provided with a weakened portion where the stick can be readily broken.

A method according to one embodiment of the invention includes opening the dropper bottle assembly by unscrewing the cap, inserting the swab into the bottle, snapping the swab stick to break it, and screwing the cap back on the bottle. The bottle containing the sorbent end of the swab is then agitated by shaking it. Now the mixed sample and buffer are ready to dispense into the testing device. This is done by opening the hinged cover of the dropper cap, inverting the bottle and dispensing the appropriate number of drops onto the device by gently squeezing the bottle.

From the foregoing, it will be appreciated that the location of the weakened portion of the swab stick is such that when the swab is placed into the bottle and touching the bottom of the bottle, the weakened portion of the stick is directly adjacent to the upper lip of the bottle neck. In this manner, the stick can be broken simply by bending it against the bottle neck with the sorbent end in the bottle.

According to a presently preferred embodiment, the hinged cover on the dripper cap has a lock which prevents it from being inadvertently opened. This prevents contamination and loss of buffer solution. The kit according to the invention preferably also contains a second bottle of buffer solution for use with a test device employing a dual path immunoassay system. Optionally, the kit includes an alcohol swab, a safety lancet, and a bandage. The kit may, and preferably does contain an immunoassay device, preferably a dual path immunoassay device. A blood collection loop is also optionally provided.

A method of testing a blood sample according to one embodiment of the invention includes using the alcohol swab to clean the area of the skin from which the sample will be taken, pricking the skin with the safety lancet, and collecting blood using the collection swab. The method then proceeds as described above.

Additional objects and advantages of the invention will become apparent to those skilled in the art upon reference to the detailed description taken in conjunction with the provided figures.

BRIEF DESCRIPTION OF THE DRAWINGS

FIG. 3 is a side elevation view of a dropper bottle assembly according to the invention;

FIG. 4 is a front elevation view of the dropper bottle assembly;

FIG. 5 is a rear elevation view of the dropper bottle assembly;

DETAILED DESCRIPTION OF THE PRESENTLY PREFERRED EMBODIMENTS

Figure 6:
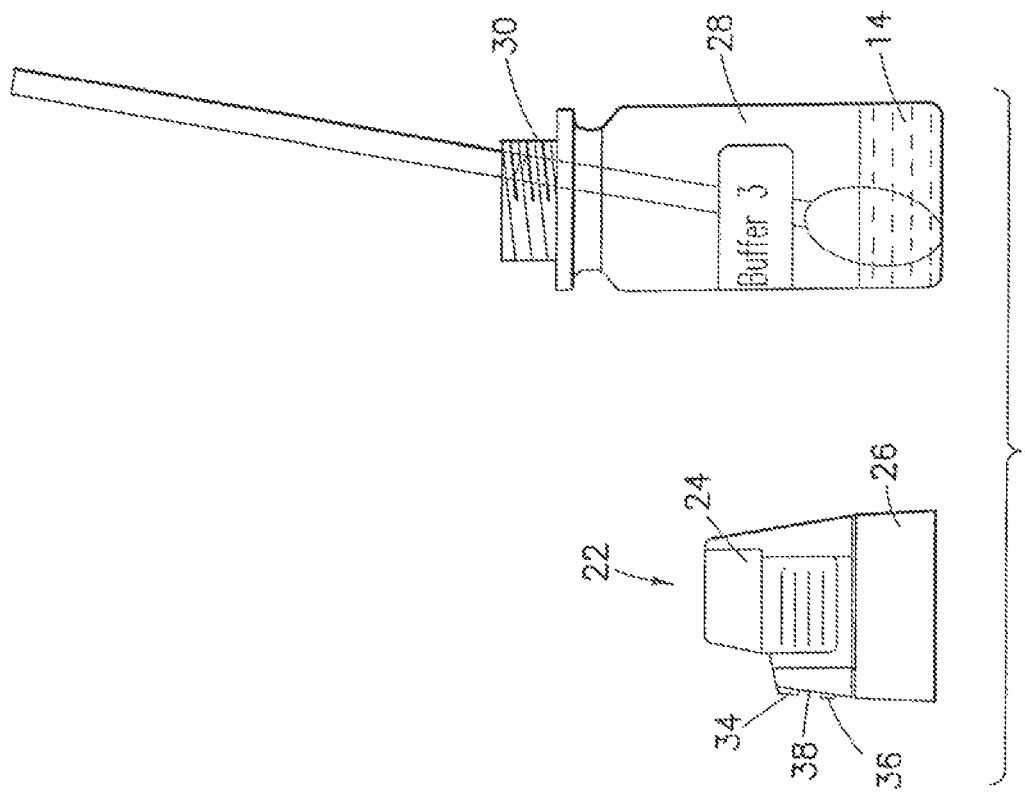
FIG. 6 is a side elevation view of the dropper bottle assembly with the cap removed and the swab inserted into the bottle.
Figure 7:
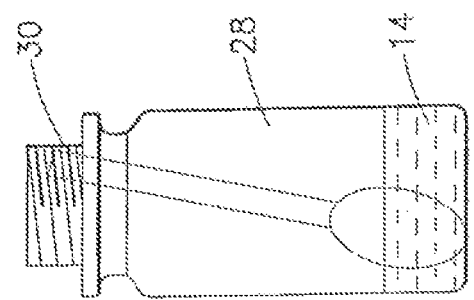
FIG. 7 is a side elevation view of the dropper bottle with the sorbent end of the swab and the stick broken.
Figure 8:
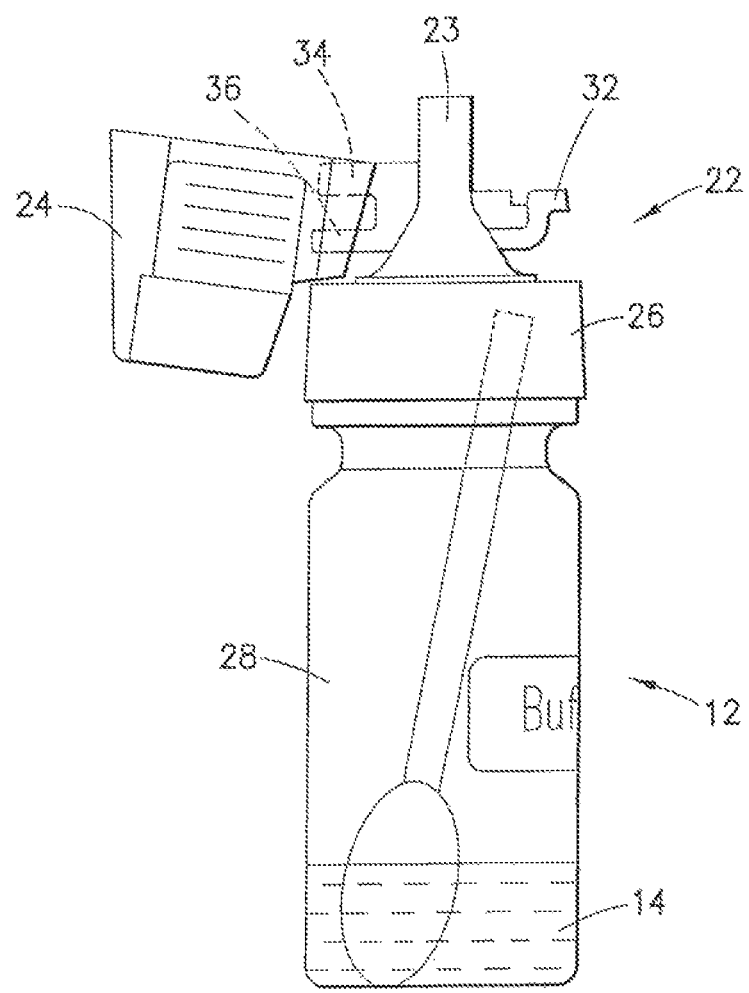
FIG. 8 is a side elevation view of the dropper bottle assembly with the sorbent end of the swab contained therein and the hinged cover opened.

Turning now to FIGS. 2-5, a kit according to the invention includes a sterile swab 10 and a dropper bottle assembly 12 containing the buffer solution 14 to which the sample is to be added. The sterile swab 10 includes a sorbent 16 mounted on the end of a stick 18. The stick 18 is preferably long enough (e.g., six inches long) so that a sample can be obtained without contaminating it. The stick is provided with a weakened portion 20 where the stick 18 can be readily broken. The dropper bottle assembly 12 includes a dropper cap 22 having a dropper spout 23, a hinged cover 24 and a threaded base 26 and a bottle 28 having a threaded neck 30 (FIGS. 6 and 7). When the kit is delivered for use, the dropper cap is threadably connected to the threaded neck of the bottle and the hinged cover is closed as shown in FIGS. 3-5.

Referring now to FIGS. 3-5 and 8, the dropper cap 22 includes a forward projecting finger 32 and two rearward projecting fingers 34, 36. The cover 24 has a rear slot which is bifurcated by a cross member 38 and a front slot which is either bifurcated or terminated by a cross member 40. As seen best in FIGS. 5, 6, and 8, the rearward projecting fingers extend into the rear slot and embrace the cross member 38 thereby forming a hinge. As seen best in FIG. 4, when the cover is closed, the forward projecting finger 32 engages the front slot above the cross member 40 and thereby prevents the cover from accidentally opening. The cover 24 is made of resilient material which can be deformed by squeezing the sides of the cover. Squeezing the sides of the cover deforms it in a manner that causes the cross member 40 to move forward and out from under the finger 32 thereby unlocking the cover and allowing it to be tiredly rotated about cross member 40 thereby opening the cover to the position shown in FIG. 8 with the spout 23 exposed. A dropper bottle assembly of the type described above is also described in U.S. Pat. No. 5,328,058 the complete disclosure of which is incorporated by reference herein.

Figure 5A:
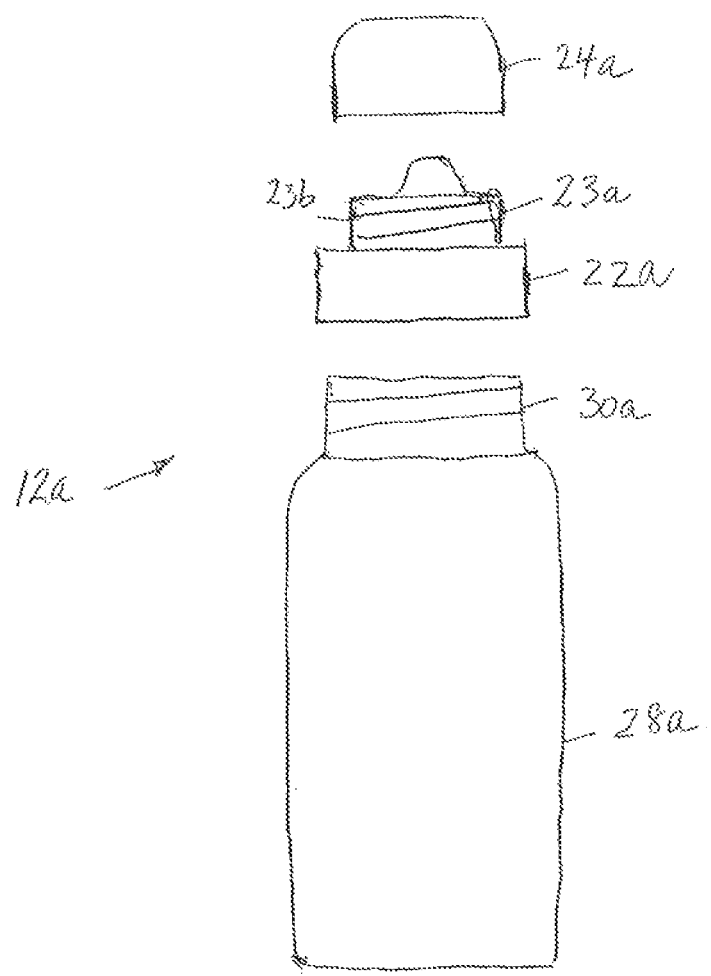
FIG. 5*a* is a front elevation view of an alternative dropper bottle assembly.

An alternative dropper bottle assembly 12*a* useful in of bottle assembly 12 is seen in FIG. 5*a*. Dropper bottle assembly 12*a* includes a bottle 28*a* having a threaded neck 30, a dropper cap 22 having internal threads (not shown) for mating with threaded neck 30 and a spout 23*a* having a neck 23*b* with external threads, and a cover 24*a* with internal threads (not shown) for mating with the threads of neck 23*b*. As will be appreciated, cap 22*a* and cover 24*a* can be removed together from bottle 28*a*, and cover 24*a* can be removed separately from cap 22*a*.

Figure 9:
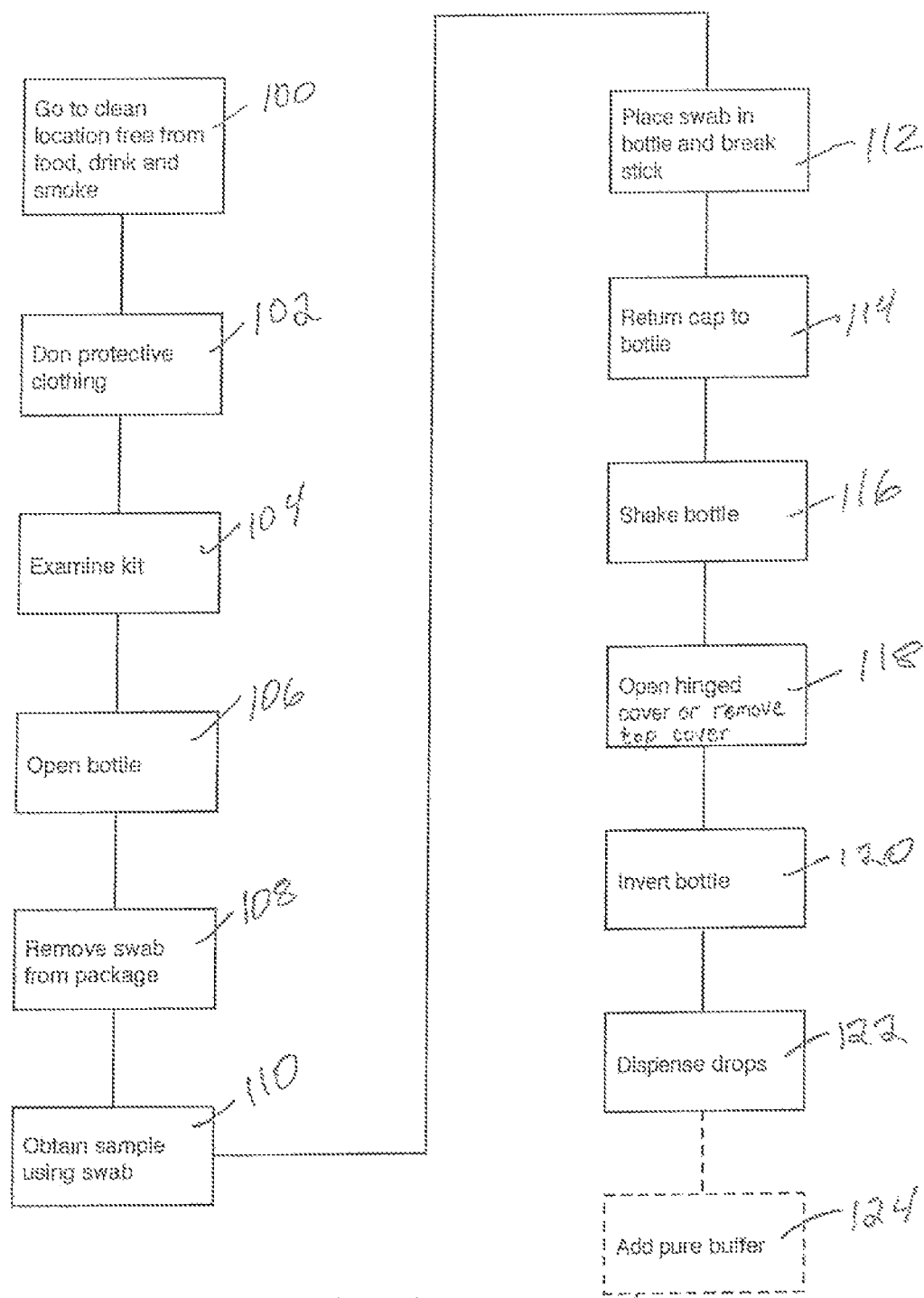
FIG. 9 is a flow chart illustrating the method steps of the invention.

A method according to the invention is illustrated in FIG. 9. The method is preferably performed in a clean room which is free from food, drink, and smoke as illustrated at 100. Optimally, the person performing the method may don protective clothing such as a face mask and rubber gloves as indicated at 102. Before beginning the method, the kit should be examined at 104 to determine whether it has expired or been contaminated through a broken package. The method then proceeds by opening up the kit and then opening the dropper bottle assembly at 106 by unscrewing the cap 22 (or cap 22*a* plus cover 24*a*) and preferably placing the bottle and the cap (or cap plus cover) on a sterile surface. The swab is then removed from its sterile package (not shown) at 108 and is used to obtain a sample at 110 which may be oral fluid (e.g., saliva or sputum), blood, urine, stool (feces), epithelia, etc. The sorbent end of the swab is then placed into the open bottle (FIG. 6) and the stick is broken at 112 (FIG. 7) typically by leveraging the stick against the edge of the threaded neck 30 of the bottle 12 so that the weakened portion 20 of the stick is near the leveraged point and snaps. Thus, the weakened portion of the stick is preferably selected to be located at a distance from the end of the sterile swab which is approximately (i.e., plus or minus 10%) the same height as the dropper bottle assembly without its cap. The cap (or cap plus cover) is then screwed back onto the bottle at 114 with the broken-stick-swab therein and the bottle is agitated at 116, preferably by shaking it a number of times, e.g. ten. The hinged cover is then opened (FIG. 8) at 118 (or the cover 24a is removed from the cap 22a) and the bottle inverted at 120 so that the buffer reaches the spout (the bottle may be held at an angle). The bottle is positioned over the test apparatus which has been removed from its sterile package (see 11 in FIG. 10) and an appropriate number of drops are dispensed at 122 through the dropper spout 23 (or 23a) by gently squeezing the bottle. When a dual path immunoassay device is used, at 124, pure buffer from a separate bottle (discussed below) is added to another location of the test apparatus.

The apparatus of the invention was tested on one hundred patients known to be infected with HIV. The tests involved collecting oral fluid and performing the procedure described above. Ninety-seven positive test results were obtained and one indeterminate result. This compared favorably with a currently (at the time of the tests) FDA approved test which obtained ninety-eight positive test results from the one hundred patients. The apparatus of the invention was tested on twenty-five patients known to be not infected with HIV. The tests involved collecting oral fluid and performing the procedure described above. All twenty-five patients tested negative or HIV. The FDA approved test achieved the same results.

Figure 2:
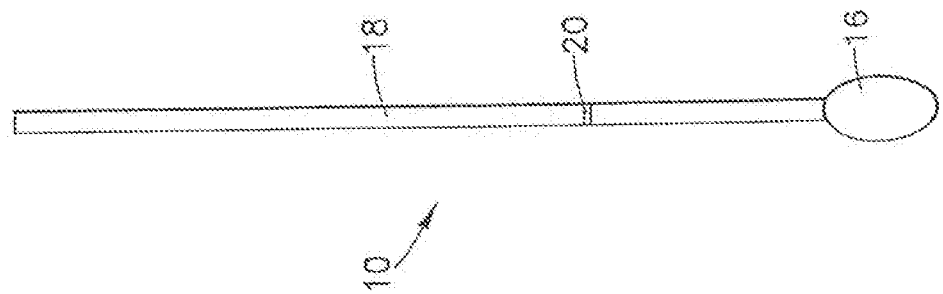
FIG. 2 is a side elevation view of a swab according to the invention.
Figure 1:
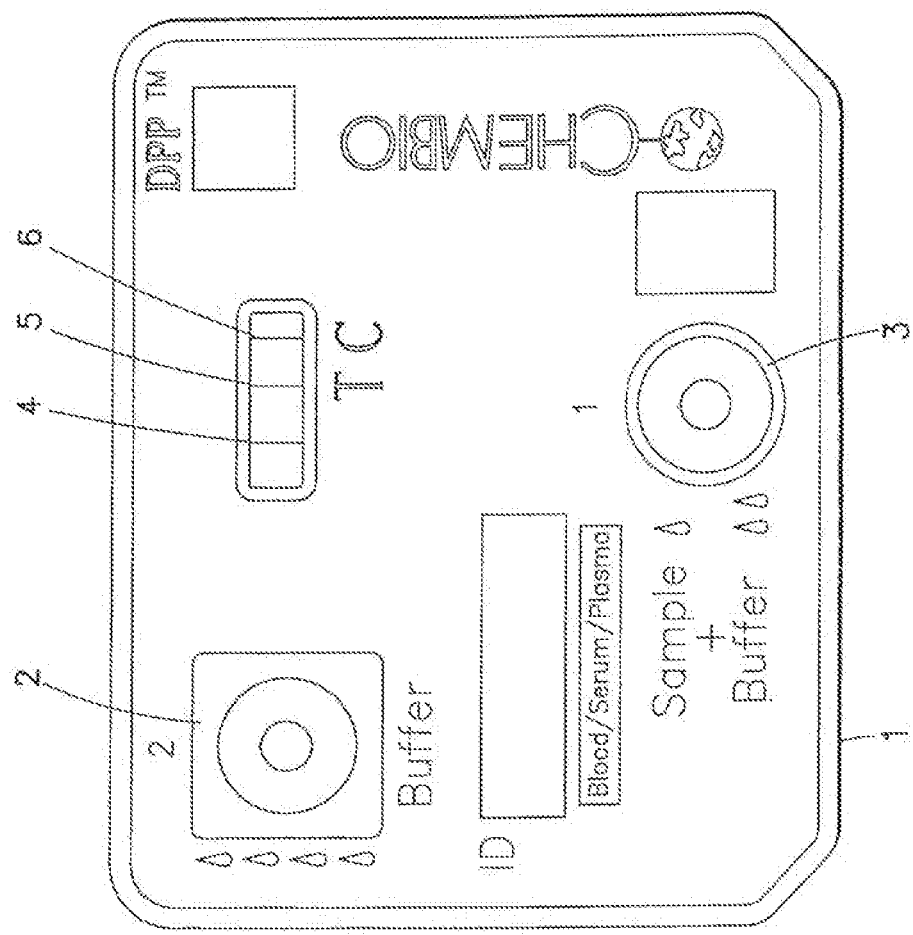
FIG. 1 is a plan view of a prior art immunoassay test device.
Figure 10:
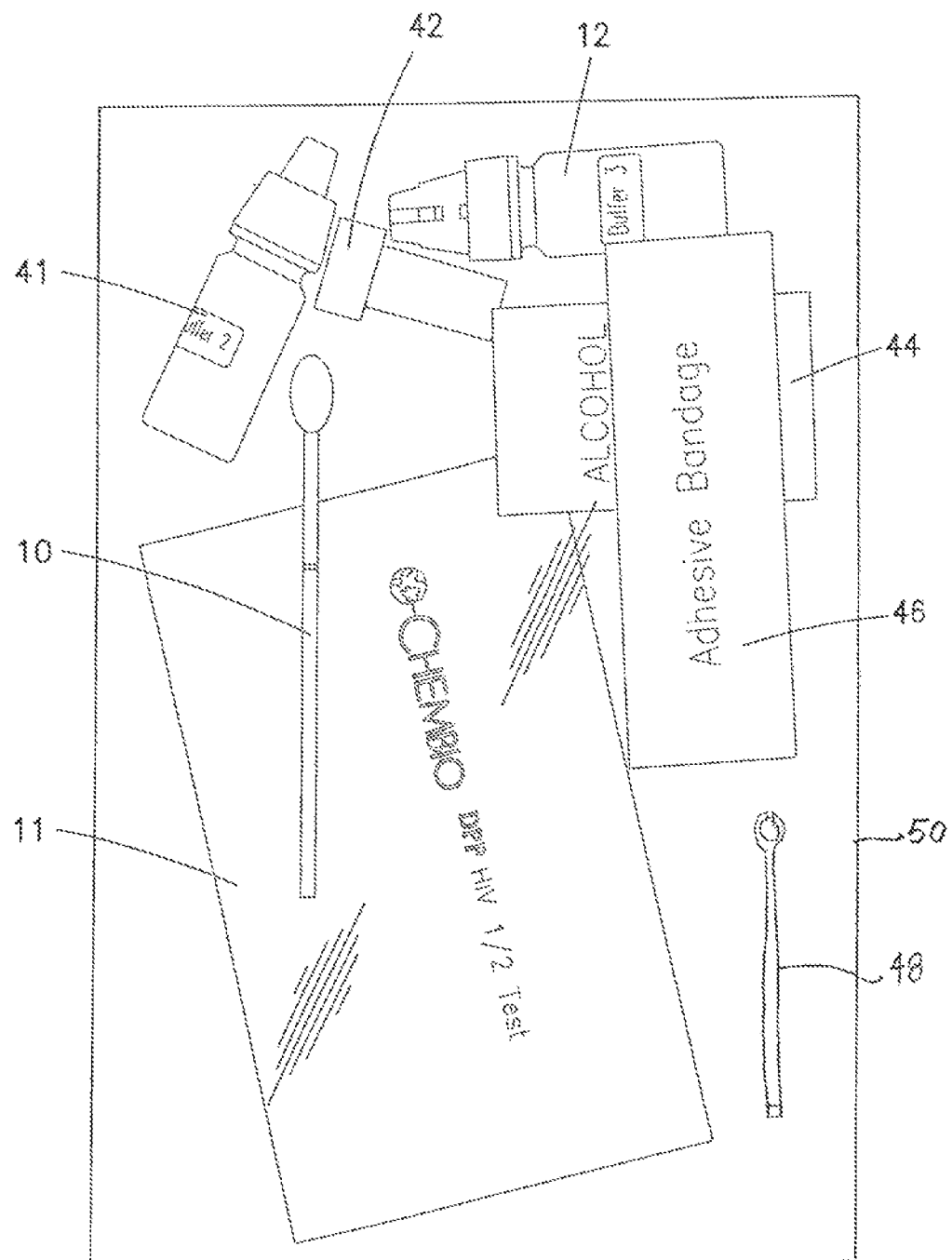
FIG. 10 is a plan diagram of an expanded kit containing a dual path test device and related sampling items.

The above described kit (with bottle 12 or bottle 12a) and method can be used with a single path assay device or with a dual path assay device. FIG. 10 shows a kit which specifically intended for use with a dual path assay device (1 in FIG. 1) which is shown in a sterile package 1. The kit includes the swab 10 which is preferably contained in a sealed sterile package (not shown) bottle assembly 12 (which can be replaced with bottle assembly 12a). The kit may also include the assay device 1 and a second dropper bottle 41 containing the buffer solution to be added to hole 2 in FIG. 1 and as shown in phantom at 124 in FIG. 9. The kit preferably further includes a safety lancet 42, a packaged alcohol swab 44 and a bandage 46. Thus, the kit contains all that is needed to test several different kinds of samples, including blood. If desired, the kit may also include a blood collection loop 48. All elements of the kit may be provided in a container or bag 50.

A method of testing a blood sample includes using the alcohol swab 44 to dean the area of the skin from which the sample will be taken, pricking the skin with the safety lancet 42, collecting blood using the collection swab 10, and bandaging the collection site with the bandage 46. The method then proceeds as described above with reference to FIG. 9. While the presently preferred embodiment of the kit and method are designed for use with a dual path immunoassay device, a kit and method for use with a single path device are also contemplated by the invention. When applied to a single path device, the kit need not contain the second dropper bottle 41.

As previously mentioned, if desired the kit of FIG. 10 may also include a blood collection loop 48. If a blood collection loop is used to collect a blood sample, the blood sample in the loop may be transferred to the assay device by touching the loop with blood collected therein to the sample pad at the sample opening. One or more drops of buffer may then be added. If the assay device is a dual path assay device, the blood sample is applied at the sample opening 3. Buffer from the second dropper bottle 41 (i.e., the pure or "running" buffer) is then added to the sample pad at the sample opening 3. After a period of time, a desired number of drops of buffer from bottle 41 are then added to opening 2 of the assay device 1.

There have been described and illustrated herein methods and apparatus for the collection and preparation of biological samples for testing. While particular embodiments of the invention have been described, it is not intended that the invention be limited thereto, as it is intended that the invention be as broad in scope as the art will allow and that the specification be read likewise. Thus, depending upon the assay device which is included in the kit, or with which the kit is to be used, different numbers of bottles of buffer, and different types of buffers or different types of solutions might be utilized, and the methods of use might vary. Also, depending upon the technique of the technician using the kit, it will be appreciated that different steps can performed in different order. It will therefore be appreciated by those skilled in the art that yet other modifications could be made to the provided invention without deviating from its spirit and scope as claimed.

What is claimed is:

1. A method for collecting and preparing a biological sample to be tested, comprising:

obtaining a kit comprising a sterile swab separate and distinct from a dropper bottle assembly, wherein the sterile swab has a stick with a sorbent fixed to the stick at one end of the stick, said stick having a weakened portion at a pre-selected location to facilitate breaking the stick, wherein the dropper bottle assembly comprises a dropper cap having a spout and a threaded base, a squeezable bottle with a threaded neck, and a cover that is manually removable from the dropper cap to expose the spout of the dropper cap, said bottle containing a liquid buffer and said dropper cap being coupled to said threaded neck, wherein length of the sterile swab is greater than height of the bottle without the dropper cap, and wherein the weakened portion of the stick is located a distance from the end of the sorbent, the distance being 90% to 100% of the height of the bottle without the dropper cap;

obtaining the sample with the sterile swab;

opening the dropper bottle assembly by unscrewing and removing the dropper cap from the threaded neck of the bottle;

inserting the one end of the sterile swab with the sorbent fixed thereto into the bottle;

breaking the stick of the sterile swab at the pre-selected location leaving the sorbent and a portion of the stick disposed inside in the bottle and not extending above the top of the bottle;

closing the dropper bottle assembly by re-screwing the dropper cap onto the threaded neck of the bottle with the stick of the swab disengaged from the dropper cap;

agitating the bottle to mix the sample with the liquid buffer contained within the bottle;

after closing the dropper bottle assembly and agitating the bottle, removing the cover from the dropper cap to expose the spout of the dropper cap; and rotating the bottle so that mixed sample and liquid buffer contents of the bottle reach the spout of the dropper cap, and squeezing the bottle to dispense at least one drop of the mixed sample and liquid buffer contents of the bottle through the spout of the dropper cap.

2. A method according to claim 1, wherein:
said agitating is accomplished by shaking the bottle multiple times.

3. A method according to claim 1, wherein:
the cover is connected to the dropper cap by a hinge that permits the cover to rotate about the hinge relative to the dropper cap, wherein said removing the cover from the dropper cap comprises rotating the cover about the hinge.

4. A method according to claim 1, wherein:
the cover is connected to the dropper cap by a thread interface, wherein said removing the cover from the dropper cap comprises rotating the cover relative to the dropper cap to remove the cover from the dropper cap.

5. A method according to claim 1, wherein:
said sample is a blood sample.

6. A method according to claim 1, wherein:
said sample is one of oral fluid, blood, urine, stool, and epithelia.

7. A method according to claim 1, wherein:
said squeezing the bottle dispenses at least one drop of the mixed sample and liquid buffer contents of the bottle to a predefined location of a test device.

8. A method according to claim 7, wherein:
the test device comprises an immunoassay device having an opening at the predefined location, wherein the opening of the immunoassay device is configured to receive the mixed sample and liquid buffer contents of the bottle.

9. A method according to claim 1, further comprising:
obtaining an additional bottle containing buffer solution; and
dispensing at least a portion of the buffer solution of the additional bottle.

10. A method according to claim 9, wherein:
said squeezing the bottle dispenses at least one drop of the mixed sample and liquid buffer contents of the bottle to a predefined first location of a test device; and
said dispensing at least a portion of the buffer solution of the additional bottle supplies the buffer solution of the additional bottle to a predefined second location of the test device, wherein the second location is spaced from the first location.

11. A method according to claim 10, wherein:
the test device comprises an immunoassay device having a first opening at the first location and a second opening at the second location, wherein the first opening of the immunoassay device is configured to receive the mixed sample and liquid buffer contents of the bottle, and wherein the second opening of the immunoassay device is configured to receive the buffer solution of the additional bottle.

* * * * *